United States Patent
Takehara et al.

(10) Patent No.: US 6,643,543 B2
(45) Date of Patent: Nov. 4, 2003

(54) BODY WATER AMOUNT CONDITION JUDGING APPARATUS BY MULTI-FREQUENCY BIOELECTRIC IMPEDANCE MEASUREMENT

(75) Inventors: Katsumi Takehara, Tokyo (JP); Tomoko Takehara, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/918,793

(22) Filed: Aug. 1, 2001

(65) Prior Publication Data

US 2002/0022787 A1 Feb. 21, 2002

(30) Foreign Application Priority Data

Aug. 1, 2000 (JP) ........................................ 2000-232703

(51) Int. Cl.$^7$ ................................................ A61B 5/05
(52) U.S. Cl. ...................................................... 600/547
(58) Field of Search ................................. 600/547, 135, 600/147, 148, 222

(56) References Cited

U.S. PATENT DOCUMENTS

| | | |
|---|---|---|
| 5,086,781 A | 2/1992 | Bookspan |
| 5,449,000 A | 9/1995 | Libke et al. |
| 5,817,031 A * | 10/1998 | Masuo et al. ................ 600/484 |
| 6,125,297 A * | 9/2000 | Siconolfi ..................... 600/484 |
| 6,434,422 B1 * | 8/2002 | Tomoda et al. .............. 600/547 |

FOREIGN PATENT DOCUMENTS

| | | |
|---|---|---|
| EP | 0 865 763 A2 | 9/1998 |
| EP | 0 998 874 A3 | 5/2000 |
| JP | 11-318845 | 11/1999 |

* cited by examiner

Primary Examiner—Max F. Hindenberg
Assistant Examiner—Jonathan Foreman
(74) Attorney, Agent, or Firm—McDermott, Will & Emery

(57) ABSTRACT

A body water amount condition judging apparatus is provided wherein at least two values selected from intra-cellular water resistance, extra-cellular water resistance, a combined resistance of the intracellular and extra-cellular water resistance, and the ratio of intra-cellular and extra-cellular water are used as the judging parameters, which values are obtained based on the bioelectric impedance measured in multi-frequency bioelectric impedance measurement. Using these parameters, it is possible to judge the body water amount condition considering not only total body water amount condition, but each constituent component of body water as well.

14 Claims, 10 Drawing Sheets

```
    Parameter input
ID    : 009876
Sex:      male
Age:
Height:        cm
Body weight    kg
```

FIG. 7

Measurement Result

Ro/Re:  Ω  ECW:  ℓ
Rinf:   Ω  ICW:  ℓ
Ri:     Ω  TBW:  ℓ

Body water amount is normal

BODY WATER AMOUNT CONDITION JUDGING APPARATUS BY MULTI-FREQUENCY BIOELECTRIC IMPEDANCE MEASUREMENT

BACKGROUND OF THE INVENTION

1. Field of the Invention

The present invention relates to a body water amount condition judging apparatus for judging condition concerning the amount of body water in a living body by measuring bioelectric impedance using a multi-frequency alternating current.

2. Prior Art

Edema is a kind of morbidity, in which interstitial fluid and/or lymph accumulates at intra-cellular or extra-cellular portions and the amount of water in a body increases. Appearing edema everywhere in a whole body may be realized as a symptom of diseases such as heart disease, kidney disease, liver disease, and such like. Therefore, it is desirable that the degree of edema is measured exactly and it is utilized in diagnosing or in monitoring patients' condition.

On the other hand, dehydration is a kind of morbidity, in which water in a living body is abnormally reduced, and it often occurs in daily life when a person is exercising or when the temperature is high because a lot of water is excreted from the body by sweating and an elevated body temperature. Especially, it is said that elderly persons are apt to experience dehydration symptoms. This is because, when one becomes older, size of muscles which contain water decreases, the amount of urine increases because the function of the kidneys deteriorates, and awareness of thirsty decreases because the senses are dulled. Another reason is that the amount of water which cells require decreases.

If dehydration symptoms are left untreated, the dehydration symptoms will gradually become worse until a serious dehydration condition is occurring. Usually, it is said that, when one third of the water in a living body is lost, the body temperature regulation is disturbed. This causes the body temperature to increase, and then water in the living body is further reduced. In other words, vicious circle is created, until at last, a heat illness occurs. A heat illness includes conditions such as heat cramp, desert syndrome and heat-stroke. Sometimes all the organs in the body are affected by the heat illness. Thus it is desired that dehydration symptoms be detected exactly to avoid the risk of a heat illness.

Japanese Patent Laid-Open Publication No. Hei 11-318845 discloses an apparatus for measuring the total amount of water in a body, thus allowing edema and dehydration symptoms which a person is not aware of to be detected. This apparatus determines the total amount of body water in a living body of a subject easily by measuring a bioelectrical impedance value, thereby allowing the subject to judge his own body water condition, such as edema or dehydration symptoms, based on this measured amount of body water.

It is known that a bioelectrical impedance value changes when the body temperature changes. That is, the bioelectrical impedance value decreases when the body temperature goes up, and the bioelectrical impedance value increases when the body temperature goes down. However, said conventional apparatus, calculating the total amount of body water based on the bioelectrical impedance value, does not take into consideration this fact that the bioelectrical impedance value changes when the body temperature changes. Thus, said apparatus can not determine the total amount of body water precisely, resulting in it being unable to detect the dehydration condition precisely. For example, in a case where the total amount of body water is decreased and the body temperature is raised, and thus a dehydration condition should be detected, the bioelectrical impedance value increases when the total amount of body water is decreased, while on the other hand, the bioelectrical impedance value decreases because body temperature is raised. Thus, when the bioelectrical impedance value is measured, and then the total amount of body water is calculated based on the bioelectrical impedance value to be able to determine whether a dehydration condition has occurred or not based on this calculated total amount of body water, the dehydration condition may not be detected.

In addition, the said apparatus measures only the total amount of body water, and does not judge the body water amount condition taking each component constituting the body water, such as each amount of intra-cellular or extra-cellular fluid, into account. Therefore, the said apparatus can not judge exact and detailed body water condition.

As the said apparatus demands personal parameters of a subject, such as height, age, sex, body weight and the like, to calculate the total amount of body water based on the measured bioelectrical impedance value, the subject has to input such personal parameters into the apparatus. Thus, it is very troublesome for the subjects, especially for elderly subjects, to operate the apparatus. It is desirable for the elderly persons to be measured their total body water frequently, because it is said that elderly persons are apt to experience dehydration symptoms as described above. However, there has been a problem that the elderly persons can not obtain their total amount of body water or obtain them based on wrongly input personal parameters.

Considering the above, an object of the present invention is to provide a body water amount condition judging apparatus which is capable of judging body water amount condition in detail, such as edema condition and/or dehydration condition exactly and easily.

SUMMARY OF THE INVENTION

The present invention provides an apparatus for judging body water amount condition, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprises: a multi-frequency bioelectric impedance measuring device; a calculating device; a reference value determining unit; a body water amount condition judging unit; and a display device. Said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values of the same kind based on judging parameter values calculated prior to each judging parameter of the same kind calculated in the past, said body water amount condition judging unit judges body water amount condition by comparing each calculated judging parameter value with the determined judging parameters of the kind, and said display device displays the judging result of said body water amount condition so judged.

In accordance with the preferred embodiment of the present invention, said calculating device may further calculate at least one of the values of intra-cellular water content, extra-cellular water content and total body water content.

In accordance with one embodiment of the invention, said reference value determining unit may determine that an average value of each judging parameter of the past is a reference value of a judging parameter of the same kind.

In accordance with another embodiment of the invention, said reference value determining unit may further determine that the latest value in judging parameters of the past is a reference value of a judging parameter of the same kind.

In accordance with another embodiment of the invention, said reference value determining unit may determine a reference value of a judging parameter every time the judging parameter is calculated.

In accordance with another embodiment of the invention, said reference value determining unit does not use a value of a judging parameter for determining a reference value of the judging parameter, when the value of the judging parameter is abnormal.

In accordance with another embodiment of the invention, said reference value determining unit may determine that a value of a judging parameter is abnormal, when the difference between each value of the judging parameter and a reference value of the judging parameter of the same kind which is already determined exceeds the predetermined value.

In accordance with another embodiment of the invention, said reference value determining unit determines whether a value of a judging parameter is abnormal or not depending upon the time a bioelectric impedance value is determined for calculating the value of the judging parameter. In accordance with another embodiment of the invention, said apparatus further comprises an abnormal value selecting device, said abnormal value selecting device decides whether a subject uses a value of a judging parameter for determining a reference value or not, and said reference value determining unit determines whether the value of the judging parameter is abnormal or not responding to said abnormal value selecting device.

In accordance with yet another embodiment of the invention, said reference value determining unit decides that a value of a judging parameter is abnormal if the time a bioelectric impedance value is determined for calculating the value of the judging parameter is in the hour of rising for the subject.

Other objects and advantages of the present invention will be understood from the following description of some preferred embodiments, which are shown in accompanying drawings:

FIG. 7 illustrates a screen image in displaying results;

DESCRIPTION OF PREFERRED EMBODIMENTS

Figure 1:
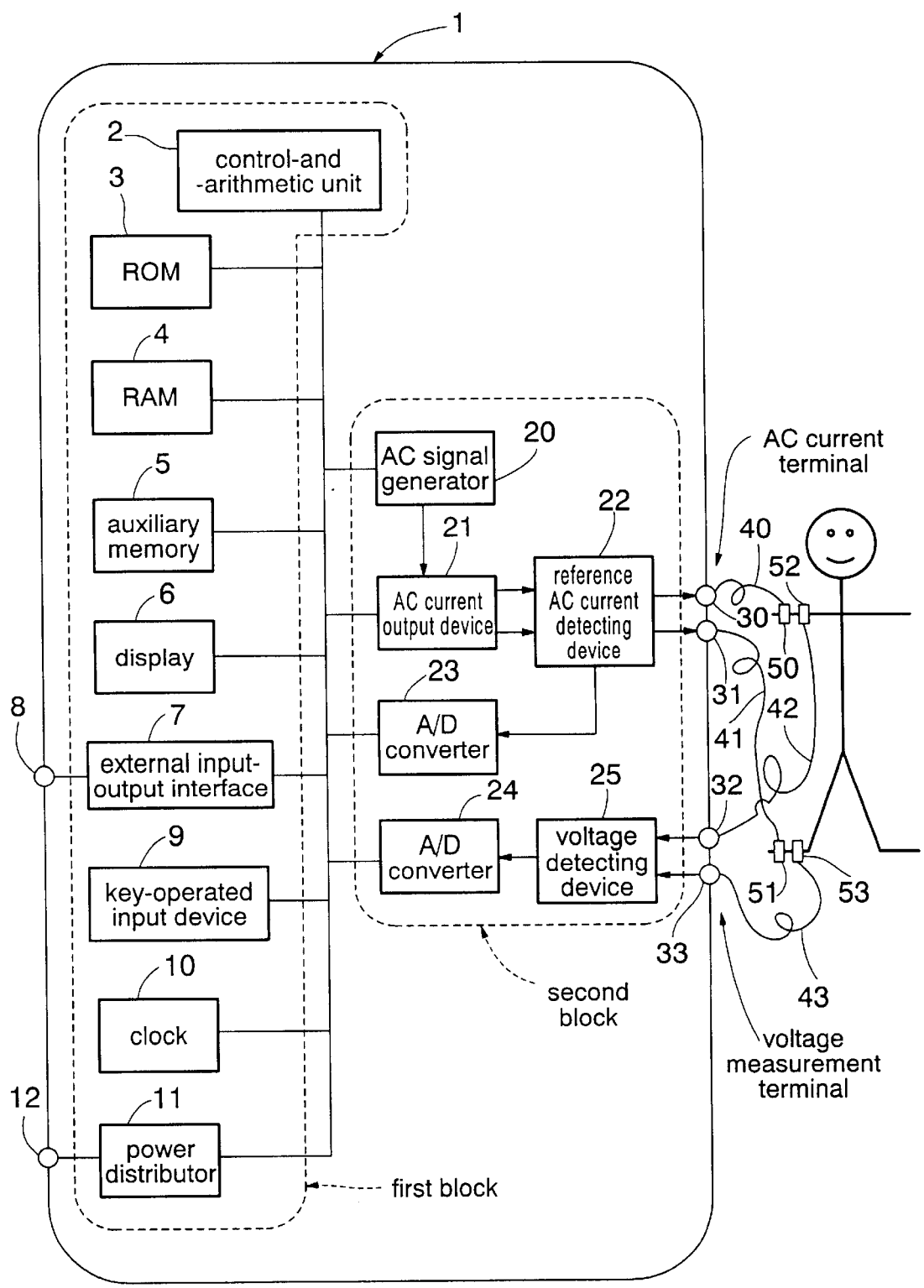
FIG. 1 is a block diagram of a body water amount condition judging apparatus according to the first embodiment of the present invention.

Preferred embodiments of the present invention will now be described in the following description. FIG. 1 is a block diagram of a body water amount condition judging apparatus according to the first embodiment of the present invention. As shown in FIG. 1, the body water amount condition judging apparatus 1 according to the present embodiment can be divided into two blocks.

The first block is a block for mainly conducting control and operation concerning measurement, and for inputting and outputting data. The first block comprises a control-and-arithmetic unit 2, a ROM 3, a RAM 4, a nonvolatile auxiliary memory 5, a display 6, an external input-output interface 7, an external interface terminal 8, a key-operated input device 9, a clock 10, a power distributor 11 and a power supply terminal 12. The control-and-arithmetic unit 2 performs the controlling of measurement and the processing of the results of measurement. The ROM 3 stores programs and some parameters for control and arithmetic operations of the apparatus 1. The RAM 4 temporarily stores the results of measurement or acquired data, the results of arithmetic operations, the data derived from external devices, selected programs and such like. The auxiliary memory 5 stores the acquired data, the results of arithmetic operations, some parameters relating to measurements and such like. The display 6 shows some helpful guidance of operation, the progressing of measurement, the results of measurements, the results of arithmetic operations and such like. The external input-output interface 7 permits some parameters relating to measurement and the results of measurements to be transferred to external devices, and inversely it permits some parameters relating to measurement, instructions for controlling measurement, control programs and such like to be supplied from external devices. The external input-output interface 7 can be connected to given external devices via the external interface terminal 8. The key-operated input device 9 inputs data such as instructions for controlling the present apparatus and personal particulars required for measurement. The clock 10 measures on what day and time each measurement is made, recording such day and time for later use. The power distributor 11 is supplied with electric power from an external power supply via the terminal 12 to distribute the electric power to each component of the apparatus.

The second block is a block for mainly impedance measuring and for converting the measured analog signal into digital signal, and includes an AC signal generator 20, an AC current output device 21, a reference AC current detecting device 22, paired AC current output terminals 30 and 31, a A/D converter 23, paired voltage measurement terminals 32 and 33, a voltage detecting device 25 and a A/D converter 24. The AC signal generator 20 provides a plurality of alternating current signals of different frequencies which are determined according to the control program stored in the ROM 3 or the RAM 4. Such alternating currents of different frequencies are directed to the AC current output device 21, in which their effective values are modified according to the control program stored in the ROM 3 or the RAM 4, and then the so modified alternating currents are directed to the reference AC current detecting device 22. The device 22 provides the alternating currents of different frequencies sequentially at its output terminals 30 and 31. The analogue value as the output of the device 22 is converted to a corresponding digital value in the A/D converter 23. On the other hand the voltage detecting device 25 receives at its input terminals 32 and 33 a signal representing the voltage appearing between two points selected on the body. Thus, the voltage is detected in the voltage detecting device 25, and the so detected voltage is converted to a corresponding digital value in the A/D converter 24.

A pair of measurement current applying electrodes 50 and 51 is connected via a pair of measurement cables 40 and 41 to a pair of AC current output terminals 30 and 31, and a voltage measurement electrodes 52 and 53 is connected via a pair of measurement cables 42 and 43 to a pair of voltage measurement terminals 32 and 33. As the apparatus 1 measures bioelectric impedance between two points selected on one hand and one foot of a subject, each electrode 50, 51, 52 and 53 is applied to a predetermined point on the subject. That is, one of the measurement current applying electrodes 50 is applied to a selected inter-finger joint point of the back of the hand and the other electrode 51 is applied to a selected inter-finger joint point of the instep of the foot. And one of the voltage measurement electrodes 52 is applied to a selected point of the wrist and the other electrode 53 is applied to a selected point of the ankle.

Figure 2:
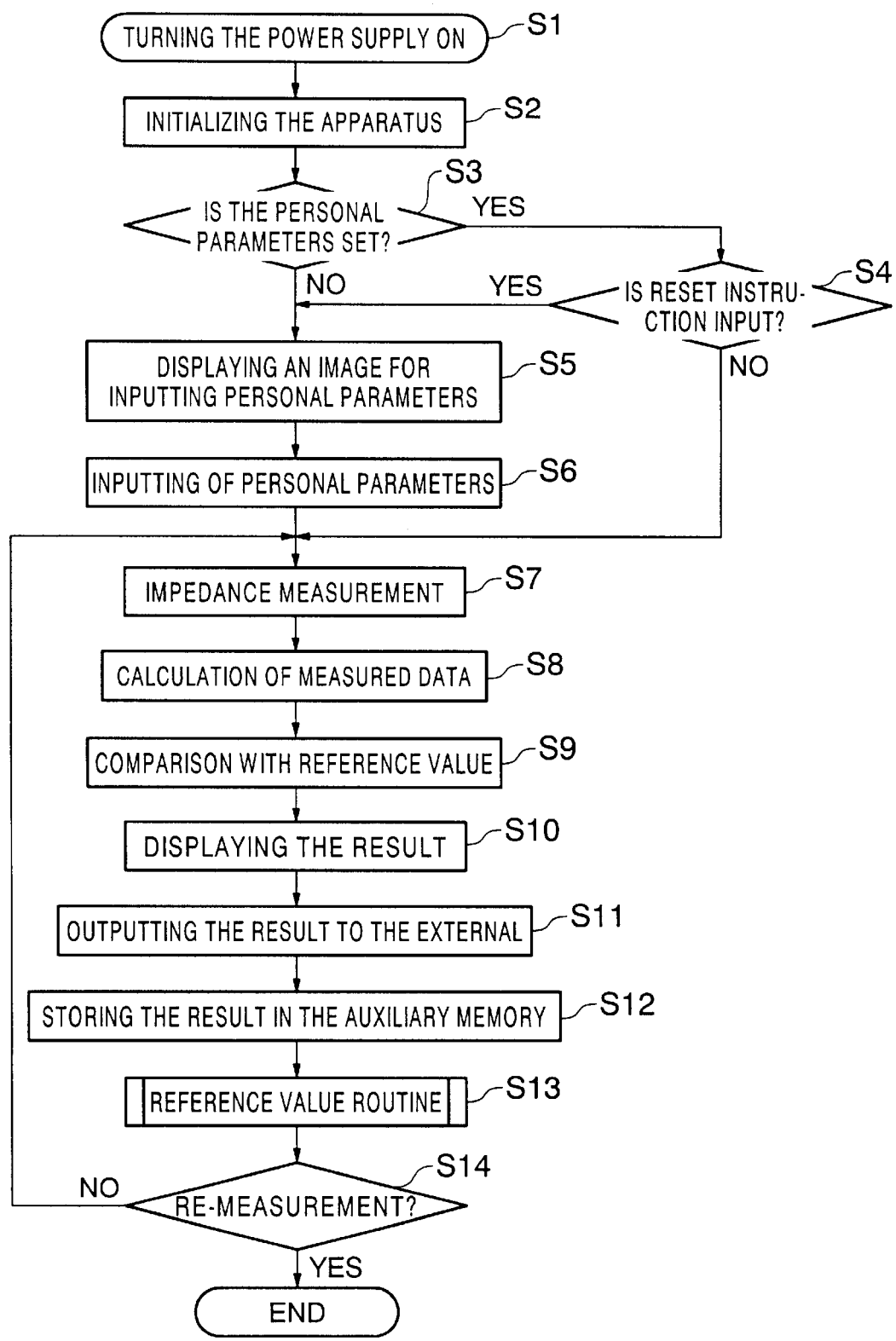
FIG. 2 is a flow chart illustrating an action flow of the body water amount condition judging apparatus shown in FIG. 1.

The operation of the judging apparatus now will be described. FIG. 2 shows a flowchart illustrating a series of actions taken in the first embodiment. When the power switch is depressed (step 1), the apparatus 1 is initialized to its initial state (step 2) and the screen image for asking the subject to input his own ID number is displayed on the display. When an ID number is input, the apparatus 1 judges whether or not the ID number is stored in the auxiliary memory 5 as the one for a subject whose personal parameters are already set. The ID number is a number which is allocated for a new subject, every time when the new subject inputs his or her personal parameters at step 6 described later, and the apparatus 1 stores these personal parameters, measurement results, operational results, judgement results and the like associated with the above ID number into the auxiliary memory 5 and manages such information for each subject, although the detailed operations of which are omitted here. When the input ID number is not the one for a subject whose personal parameters are already set, then the apparatus 1 displays the message on the display 6 saying that the input ID number is not correct and the subject should input his or her correct personal parameters again (step 6). When the input ID number is the one for a subject whose personal parameters are already set, then the apparatus 1 further judges whether or not the reset instruction is input by the subject through the key-operated input device 9 (step 4). In case the reset instruction is input or the input ID number is not the one for a subject whose personal parameters are already set, the apparatus 1 displays an image shown in FIG. 3 for inputting personal parameters and waits for inputting (step 5). When a subject inputs his sex, age, height and body weight as his personal parameters, if he or she is a new subject, the apparatus 1 allocates a new ID number for him or her, and displays it on the display 6 (step 6). When the inputting operation of the personal parameters completes or in case the reset instruction is not input at the step 4, the apparatus 1 is changed to its standby condition. After the electrodes 50, 51, 52 and 53 are applied to the predetermined point on the subject's body and the instruction for starting measurement is input through the key-operated input device 9, the apparatus starts measurement for multi-frequency bioelectric impedance.

Now, the measurement for multi-frequency bioelectric impedance will be explained briefly. In this measurement, n different frequencies Fi (i=1, 2, . . . , n and n is a predetermined value) are used and the bioelectric impedance is measured n times for each frequency Fi.

Initially, the "i" is set to 1, and the first measurement of bioelectric impedance for frequency F1 is started. That is, output signal frequency is set in the AC signal generator 20 based on a measurement control parameter previously stored in the ROM 3 or a measurement control parameter stored in the auxiliary memory 5 or the RAM 4 through the external input-output interface, and the output signal having the set frequency is output to the AC current output device 21 from the AC signal generator 20. The AC current output device 21 is composed of a constant-current outputting circuit which is capable of setting its current value. An output current value is set in the AC current output device 21 based on the measurement control parameter, and an AC current output having the output current value is supplied from the AC current output device 21 to a subject through the reference AC current detecting device 22, the AC current output terminals 30 and 31, the measurement cables 40 and 41, and the electrodes 50 and 51 which are applied to the subject.

The reference AC current detecting device 22 detects a current flowing through the subject during the AC current output is supplied to the subject. The detected analog signal is output to the A/D converter 23, converted to digital signal and then stored in the RAM 4.

Electric potentials at two points on the subject where the electrodes 52 and 53 are applied is detected during the current is supplied to the subject. The detected values are input to the voltage detecting device 25 through the measurement cables 42 and 43, and the measurement terminals 32 and 33. Then a potential difference signal which is a difference between the two input potential values is output from the voltage detecting device 25, and this analog output signal is converted to a digital signal by the A/D converter 24. The digital signal is utilized by the control-and-arithmetic unit 2 to derive a bioelectric impedance, and the derived bioelectric impedance value is stored in the RAM 4.

Next, i is incremented to i+1 (i=i+1) and it is judged whether or not the i exceeds a predetermined value n. If the i exceeds the n, then the overall measurement of the bioelectric impedance is completed. On the other hand, if the i does not exceed the n, the next measurement of the bioelectric impedance for a new frequency will be conducted (step 7).

Following the above multi-frequency bioelectric impedance measurement, the judging apparatus 1 calculates a locus of bioelectrical impedance vectors and a parameters thereof based on bioelectric impedance values measured for each of a plurality of different frequencies.

Figures 3, 4:
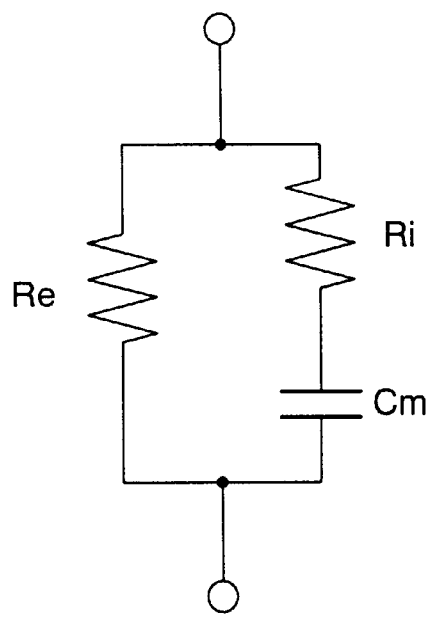
FIG. 3 illustrates a screen image in inputting personal parameters.
FIG. 4 is an electrically equivalent circuit of cells in a living body.
Figure 5:
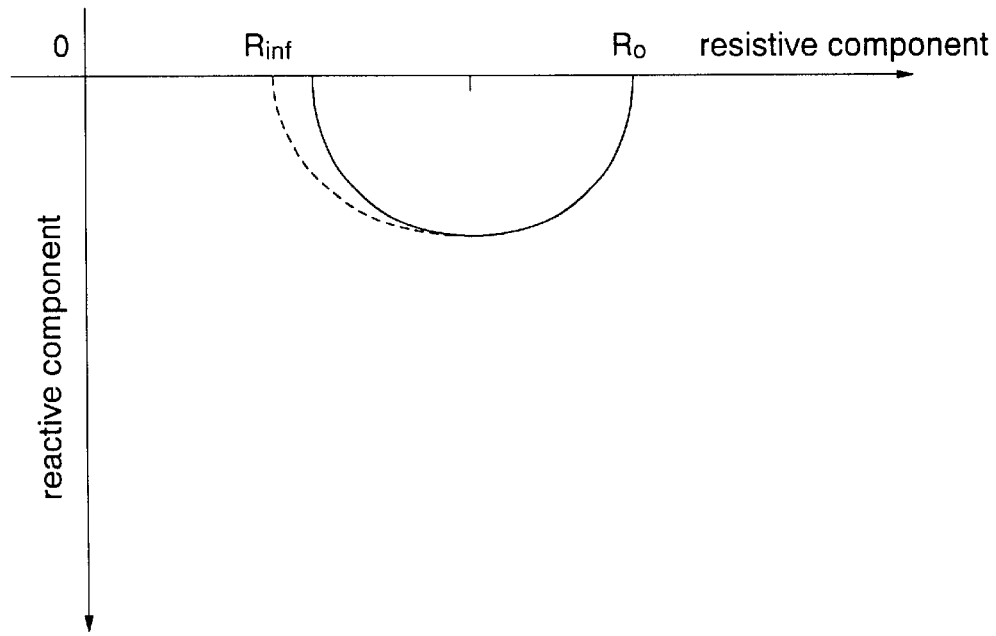
FIG. 5 is a vector locus of bioelectric impedance of a human body.

Now the method for calculating the locus of bioelectrical impedance vectors and the parameters will be explained briefly. Ordinarily a bioelectrical impedance can be expressed equivalently by a lumped-constant circuit, which consists of extra-cellular water resistance Re, intra-cellular water resistance Ri, and cell membrane capacitance Cm as shown in FIG. 4. The locus of bioelectrical impedance values actually measured, however, is not in conformity with a semicircular locus drawn theoretically from the impedance values, which are determined from the equivalent circuit whose components are given in the form of lumped constant elements. Because all cells of a living body cannot be expressed by one and same equivalent circuit; specifically each cell has a different shape and characteristic, and should be expressed by a different equivalent circuit allotted only to the same, particular cell for exclusive use. As a matter of fact, the locus of bioelectrical impedance vectors actually measured is given by an arc determined according to Cole—Cole model. One example of arc-like locus determined from Cole—Cole model is shown in FIG. 5, in which the horizontal axis and the vertical axis represent the resistive component and reactive component of the bioelectrical impedance respectively. As the reactive component of the bioelectrical impedance is capacitive, and is given by a negative value, the locus of bioelectrical impedance is located below the X-axis as shown in FIG. 5.

Figure 6:
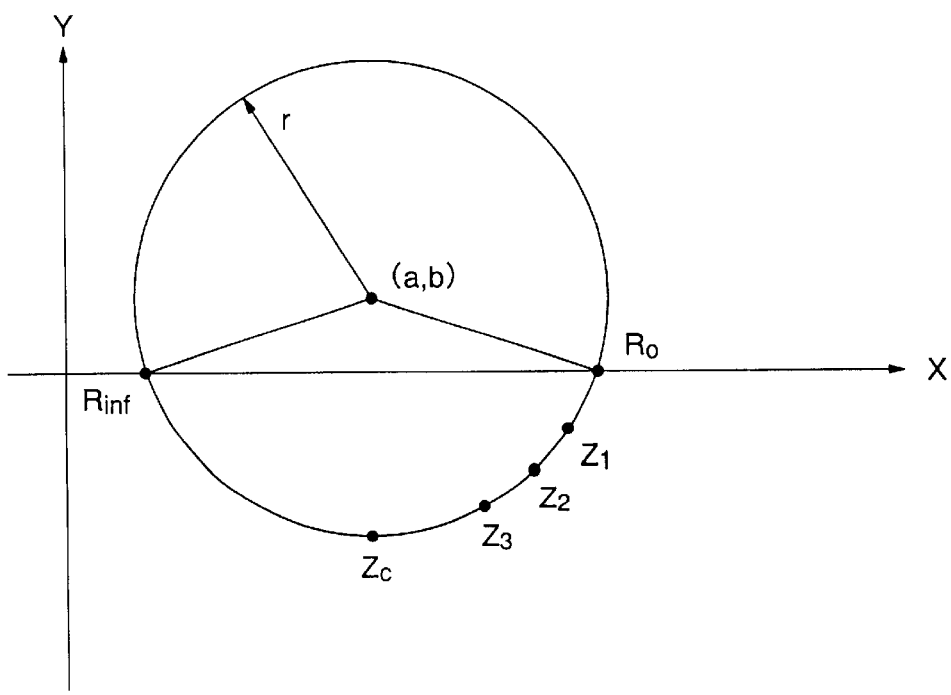
FIG. 6 illustrates a relation between bioelectric impedance at zero frequency and at infinite frequency and bioelectric impedance at characteristic frequency.

As the calculated locus of bioelectrical impedance is assumed to be in conformity with circular arc shape, the points of bioelectrical impedance $Z_1, Z_2, \ldots, Z_N$ measured in terms of frequencies Fi are located as shown in FIG. 6. In the following, let us assume that the horizontal axis as a real axis is a X-axis and the vertical axis as imaginary axis is a Y-axis in a impedance vector plane.

The following correlation function (1) is derived from the Zi (I=1 to n) plotted on the coordinate system:

$$(X-a)^2+(Y-b)^2=r^2 \quad (1)$$

where "a" and "b" are the abscissa and ordinate of the center of the circle, "r" stands for the radius of the circle, and the equation (1) represents an approximate correlation function based on n points. Equation (1) is rewritten in terms of "X":

$$X=a\pm\sqrt{(r^2-b^2)}$$

and as R0>Rinf, $$R_0=a+\sqrt{(r^2-b^2)}$$

$$R_{inf}=a-\sqrt{(r^2-b^2)}$$

is obtained. Therefore, Re and Ri of an equivalent circuit in FIG. 4 can be given as follows:

$$Re=R0$$

$$Ri=R0 \cdot Rinf/(R0-Rinf)$$

From the above calculation, combined resistance of the intra-cellular and extra-cellular water resistance Rinf (=Ri// Re), extra-cellular water resistance Re and intra-cellular water resistance Ri are obtained, and therefore the ratio of intra-cellular and extra-cellular water Ri/Re is obtained. It should be noted that there is no need for personal parameters, such as height, age, sex, body weight and the like, to obtain these values.

An intra-cellular water content ICW, an extra-cellular water content ECW, a ratio of the intra-cellular water content to the extra-cellular water content ICW/ECW, a total body water content TWB (=ICW+ECW) and the like can be calculated based on the obtained locus of bioelectrical impedance vectors, parameters R0 and Rinf or Re and Ri concerning thereof, and the parameters of height, age, sex and body weight which are input at step 3, through an already known method. For example, the intra-cellular water content ICW, the extra-cellular water content ECW, and the total body water content TWB are calculated through the following equations using Ri, Re, height Ht, and body weight W:

$$ICW=K_{i1}Ht^2/Ri+K_{i2}W+K_{i3}$$

$$ECW=K_{e1}Ht^2/Re+K_{e2}W+K_{e3}$$

$$TBW=ICW+ECW$$

Where $K_{i1}$, $K_{i2}$, $K_{i3}$, $K_{e1}$, $K_{e2}$ and $K_{e3}$ are coefficients.

Then the judging apparatus 1 judge a body water amount condition at the time when the bioelectric impedance is measured at step 7. Assuming that the intra-cellular water resistance Ri and the ratio of intra-cellular and extra-cellular water resistance Ri/Re are the judging parameters, this judging operation is conducted by comparing each value of judging parameters obtained at step 7 with the reference values of judging parameters of the same kind which are stored in the auxiliary memory 5. However, if the reference values of judging parameters are not stored in the auxiliary memory 5, then the judging operation is not conducted. The reference values of judging parameters represent the values of judging parameters when the total body water content is in a normal condition, and are determined in step 13 which will be described later.

There is a relation that the intra-cellular water resistance and the extra-cellular water resistance rise when the intra-cellular water content and the extra-cellular water content decrease, and to the contrary, the intra-cellular water resistance and the extra-cellular water resistance drop when the intra-cellular water content and the extra-cellular water content increase. In addition, we suppose that both in edema condition in which the amount of water in a body increases and in dehydration condition in which the amount of water in a body reduced, the intra-cellular water resistance is little changed at their initial stages, and then the changes begin to appear in their later stages. The judging operation of the apparatus 1 is conducted under the above relation and the assumption. The assumption is derived from the fact that the changes in the amount of body water arise initially in a extra-cellular water, and thus the concentration of electrolytic solution in the extra-cellular water arises causing the concentration difference between the intra-cellular water and the extra-cellular water, and then the concentration difference is relaxed gradually by the passage of water through cell membrane under the effect of osmotic pressure.

Under the above described relation and the assumption, the judging apparatus 1 judges that it is in the early stages of dehydration symptoms if the combined resistance of the intra-cellular and extra-cellular water resistance obtained this time is a little higher than the reference value and the ratio of intra-cellular and extra-cellular water resistance obtained this time is lower than the reference value, and the judging apparatus 1 judges that it is in the later stages of dehydration symptoms if the combined resistance of the intra-cellular and extra-cellular water resistance obtained this time increases drastically above the reference value and the ratio of intra-cellular and extra-cellular water resistance obtained this time is higher than the reference value. Further, the judging apparatus 1 judges that it is in the normal condition if the combined resistance of the intra-cellular and extra-cellular water resistance obtained this time is almost the same as the reference value and the ratio of intra-cellular and extra-cellular water resistance obtained this time is also the same as the reference value.

In this way, the combined resistance of the intra-cellular and extra-cellular water resistance and the ratio of intra-cellular and extra-cellular water resistance are used as judging parameters. This means that the judging operation is conducted based not only on a condition of total amount of water in a body, but also on each constituent component of body water, that is, each condition of the amount of extra-cellular water and intra-cellular water, thereby resulting in a exact and detailed judging results.

In addition, as the combined resistance of the intra-cellular and extra-cellular water resistance and the ratio of intra-cellular and extra-cellular water resistance are obtained using the bioelectric impedance which is measured under the multi-frequency bioelectric impedance measurement, these values are not affected by body temperature, so the inaccuracy in judging the body water amount condition due to the affection of the body temperature will be effectively avoided (step 9).

When the judging operation is completed, the apparatus 1 indicates on the display device 6 each resistance value obtained in step 8 and the body water amount condition judged in step 9 and the like. FIG. 7 illustrates an example of such indication (step 10). Further, the apparatus 1 sends the measurement results, the calculation results, the judgement results, the personal parameters and the like to external devices like a monitor device, a printer or the like, under the measurement-controlling parameters through the external input-output interface 7, and also stores them into the auxiliary memory 5 (step 12).

Figure 8:
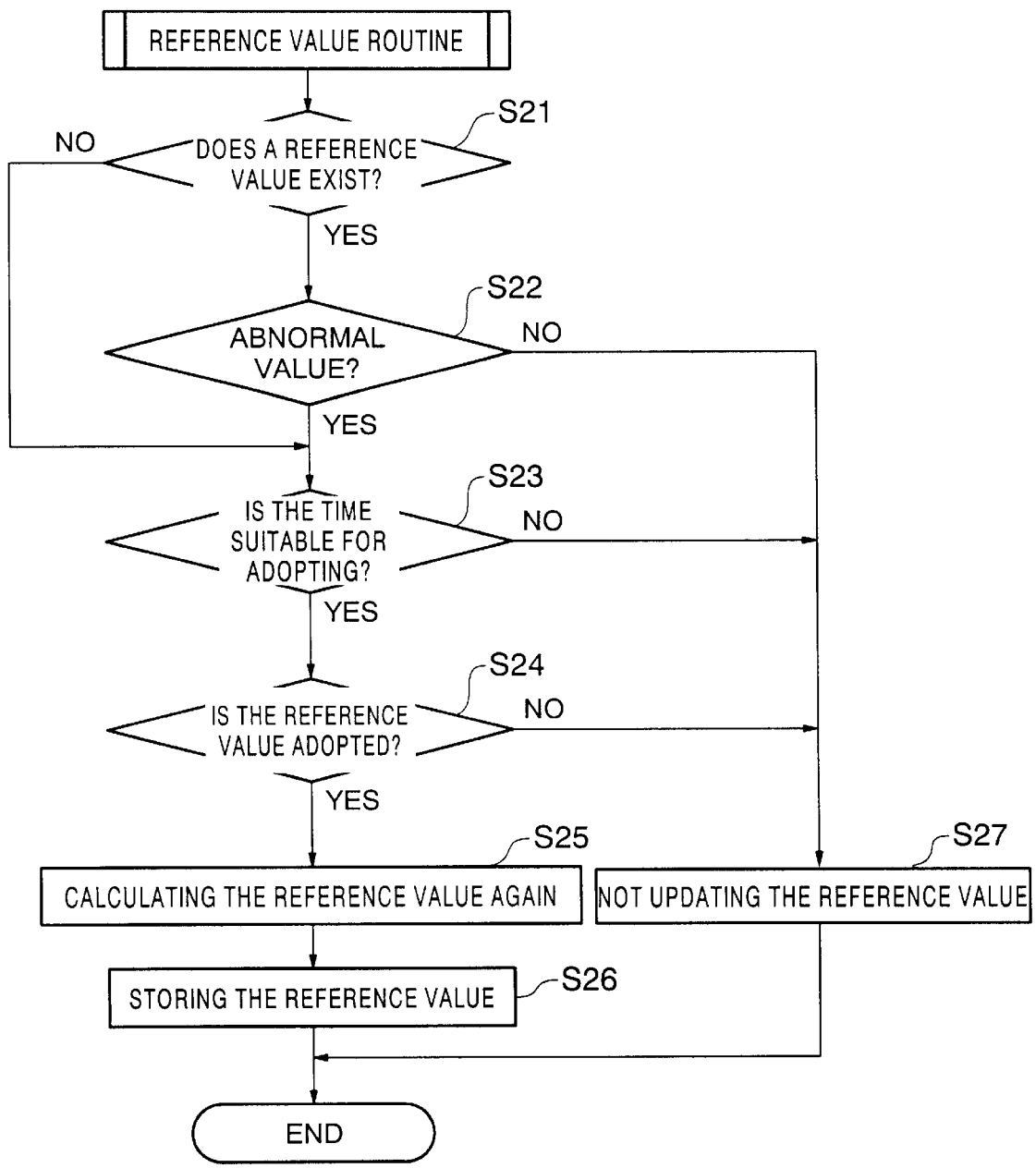
FIG. 8 is a flow diagram illustrating the process of a routine for determining a reference value.

Next, the judging apparatus 1 carries out a reference value determining process for determining reference values which are used as a judging parameters in the next judging operation (step 13). FIG. 8 is a flow chart which illustrates processes for determining the reference value. The apparatus 1 first judges whether or not reference values of each parameter are stored in the auxiliary memory 5 (step 21). When the reference values are stored, the apparatus 1 judges whether each judging parameter of this time is normal or not, by comparing each parameter calculated in step 8 with the corresponding stored reference values of the judging parameters of the same kind. The apparatus 1 compares the value of the judging parameter of this time with the reference value of the judging parameter, and if, for example, the difference between the value of the judging parameter and the reference value is 20% or more, the apparatus 1 judges that the value of the judging parameter of this time is abnormal (step 22). If the abnormal value is detected, the apparatus 1 does not use such a value of the judging parameter of this time to determine the reference value of the same kind, and does not update the reference value. In such a case, the same reference value of the judging parameter will be used again in the next judgement (step 27).

If the apparatus 1 does not detect an abnormal value in step 27 and if the apparatus 1 decides that there is no reference value in step 21, then the apparatus decides whether or not the time when the bioelectric impedance is measured to obtain the judging parameter of this time in step 7 is suitable for adopting the reference value (step 23). As a example, if the measuring time is decided to be an early time in the morning, the apparatus 1 considers the judging parameter of this time to be an abnormal value, and does not use the value to determine the reference value of the judging parameter, and does not update the reference value which has already been stored (step 27).

Further, the apparatus 1 indicates an image on the display device 6 which inquires whether or not the subject will use the judging parameter of this time to determine the reference value (step 24). If the answer which is input through the key-operated input device 9 is no, the apparatus 1 considers the judging parameter of this time to be an abnormal value, and does not use the value to determine the reference value of the judging parameter, and does not update the reference value which has already been stored (step 27).

On the other hand, if the answer which is input through the key-operated input device 9 is yes in step 24, then the apparatus 1 uses the judging parameter values of the same kind as past values, along with each past judging parameter value which was calculated until last time and had been used to determine reference values without being considered as a abnormal value from step 22 to 24 until last time. Then the apparatus 1 obtains the average value from these values and decides the obtained value as a judging parameter reference value of the same kind which will be used in the next judgement.

In this way, the reference value of judging parameters are not determined as a common value among subjects, but determined for each subject using the past values of judging parameters obtained before. Therefore, the specific reference values of judging parameters for each subject can be obtained which are not affected by the difference among individuals. In addition, since the reference values of judging parameters are determined again in the way that these values are the average values of the judging parameter values obtained in the past including the last time and abnormal values are excluded during this procedure, according as the number of times increases, the reference values of judging parameters can be obtained which indicate more exactly the body water amount in a normal condition. Therefore, it is possible to judge the body water amount condition appropriately according to each individual subject (step 25).

And then, the apparatus 1 stores the reference values of the judging parameters obtained in step 25 in the auxiliary memory 5, and closes the process for determining the reference values.

After closing the process, the apparatus 1 judges whether or not an instruction for re-measurement is input via the key-operated input device 9 (step 14). If such an instruction is input, the measurements and the judgements are conducted again from step 7. If such an instruction is not input in step 14, then a series of measurement and judgement is completed.

In this embodiment, the intra-cellular water resistance and the ratio of intra-cellular and extra-cellular water resistance, which are obtained using bioelectric impedance measured in the multi-frequency bioelectric impedance measurement in step 10, are used as judging parameters. But, at least two values selected from the intra-cellular water resistance, the extra-cellular water resistance, combined resistance of the intra-cellular and extra-cellular water resistance, and the ratio of intra-cellular and extra-cellular water may be used as judging parameters. Using these parameters, it is possible to judge the body water amount condition considering not only mere total body water amount condition, but also each constituent component of body water, that is, each amount condition of extra-cellular water and intra-cellular water. Each of these parameters is obtained from measured bioelectric impedance in the multi-frequency bioelectric impedance measurement without being affected by body temperature, and thus, inaccuracy in judging the body water amount condition due to body temperature can be effectively avoided.

Although personal parameters are input in step 6 in this embodiment, these values are necessary only for obtaining the body water amount, intra-cellular water and extra-cellular water, and are not necessary for obtaining the intra-cellular water resistance, the extra-cellular water resistance, combined resistance of the intra-cellular and extra-cellular water resistance, and the ratio of intra-cellular and extra-cellular water, which are the judging parameters in this embodiment. Therefore, it is also possible to simplify the operation of the apparatus without inputting the personal parameters.

In addition to, or in place of the process for excluding abnormal values from step 22 through 24, it is possible to obtain an average value from the judging parameter values except for maximum and minimum values which are used to obtain reference values of judging parameters.

Next, the second embodiment of the present invention will be explained. This embodiment of the body water amount condition judging apparatus is a handheld-type in which bioelectric impedance is measured between both hands of a subject. Since personal parameters are not necessary to be input in this apparatus, easier handling for judging the dehydration condition can be achieved.

Figure 9:
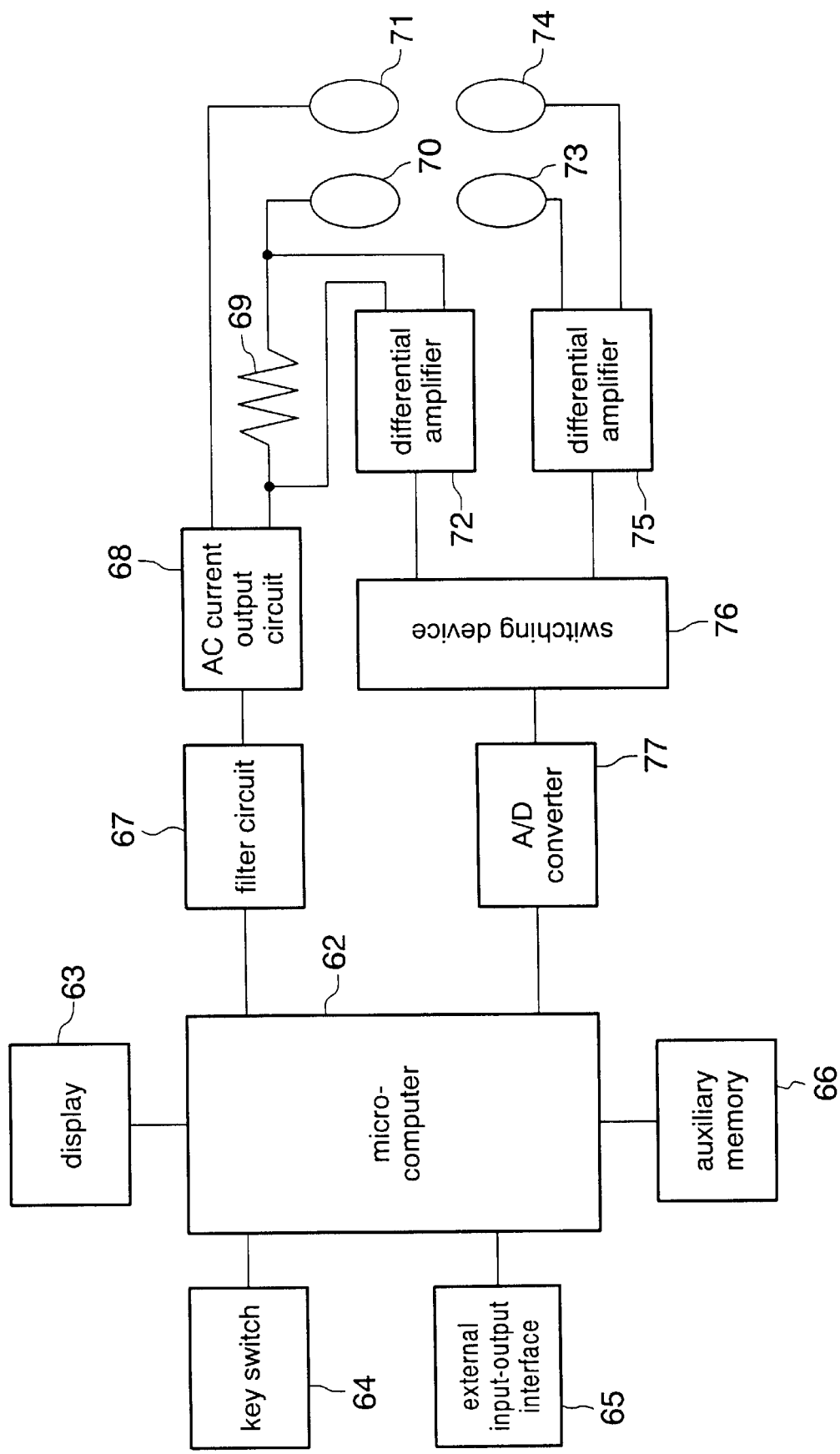
FIG. 9 is a block diagram of a body water amount condition judging apparatus according to the second embodiment of the present invention.

FIG. 9 is a block diagram of a body water amount condition judging apparatus according to the second embodiment of the present invention. As shown in FIG. 9, the dehydration condition judging apparatus 61 comprises a microcomputer 62 having a CPU, ROM, RAM, timer and I/O port. The CPU controls measurements and judgements, and processes the measurement data. The ROM stores programs and some parameters for control and calculation operations. The RAM temporarily stores the results of operations, the programs derived from external devices, selected parameters and the like.

The dehydration condition judging apparatus 61 further comprises a display 63, a key switch 64, an external input-output interface 65, a nonvolatile auxiliary memory 66. The display 63 shows progress made in the measurements and judgement results and the like. The key switch 64 inputs instructions and the like for controlling the present apparatus 61. The external input-output interface 65 permits the judgement results to be transferred to external devices, and inversely it permits instructions for controlling the device and some parameters and the like to be supplied from external devices. The parameters relating to the measurement are stored in the auxiliary memory 66. The data stored in the memory can be read out and updated.

The apparatus 61 further comprises a filter circuit 67, an AC current output circuit 68, a reference resistor 69, a measuring current supply electrode 70 and a measuring current supply electrode 71. The filter circuit 67 changes waveforms to signals to be applied to a living body. The AC current output circuit 68 modifies the signals outputted from the filter circuit 67 to a predetermined effective value. The measuring current supply electrode 70 is connected to one output terminal of the AC current output circuit 68 via the reference resistor 69. The measuring current supply electrode 71 is connected to the other output terminal of the AC current output circuit 68. Thus, AC current is applied through the measuring current supply electrodes 70 and 71.

The apparatus 61 further comprises a differential amplifier 72, voltage measuring electrodes 73 and 74, and a differential amplifier 75. The differential amplifier 72 detects a voltage difference between one terminal and the other terminal of the reference resistor 69 in order to detect a current flowing into the body of the subject. The voltage measuring electrodes 73 and 74 detect voltage at two points on the subject. The differential amplifier 75 is connected to the voltage measuring electrodes 73 and 74 to detect a voltage difference between these electrodes.

The apparatus 61 further comprises a switching device 76, an A/D converter 77. The switching device 76 outputs a selected one of the outputs of the amplifiers 72, 75 based on the control of the microcomputer 62. The A/D converter 77 converts analogue signals outputted from the switching device 76 to digital signals and then outputs them to the microcomputer 62.

Figure 10:
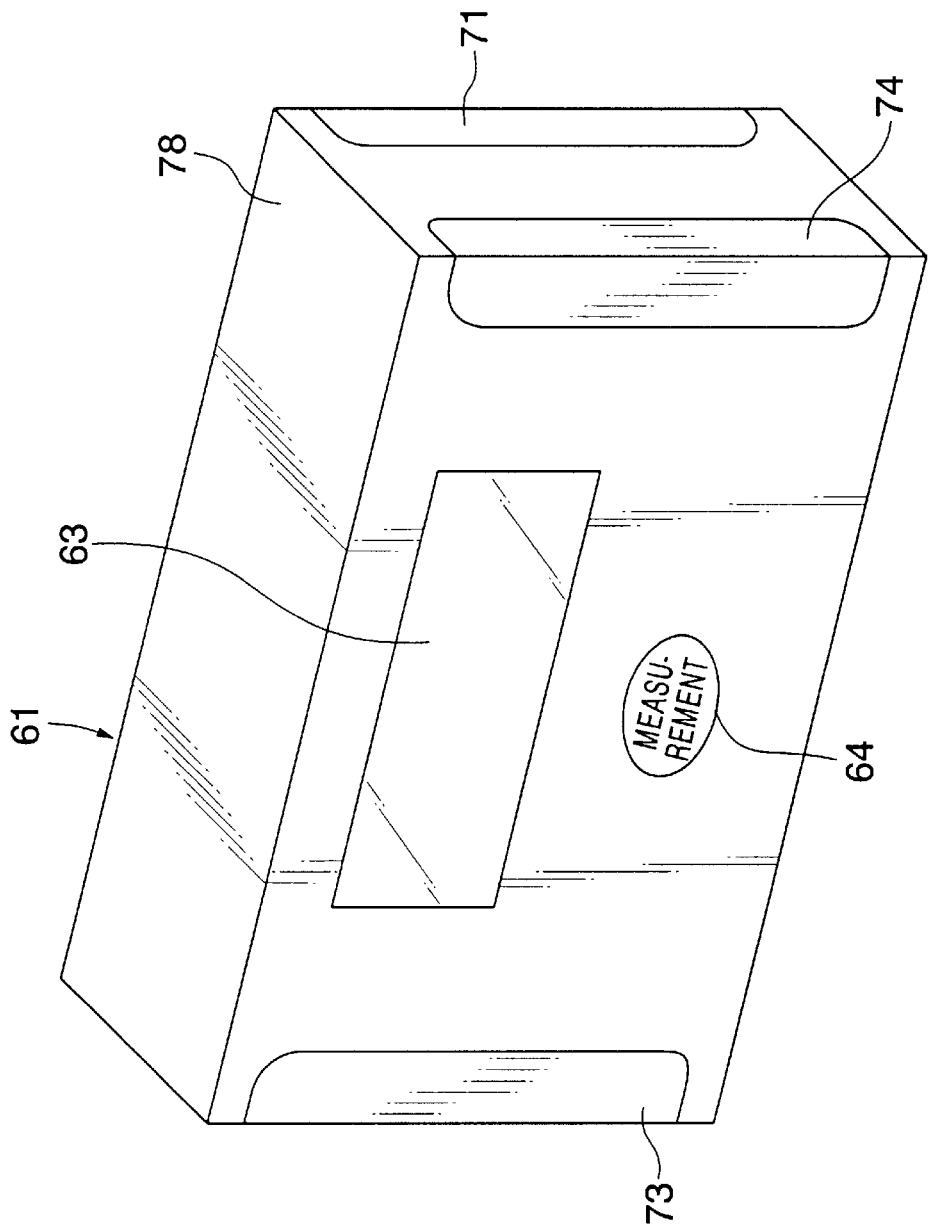
FIG. 10 is a perspective view of a body water amount condition judging apparatus shown in FIG. 9.

FIG. 10 is a perspective view of the body water amount condition judging apparatus shown in FIG. 9. As shown in FIG. 10, the apparatus 61 comprises a housing 78 which has a substantially box shape. The voltage measuring electrodes 73 and 74 and the measuring current supply electrodes 70 and 71 are disposed to be spaced apart from each other on the circumference of the housing 78. That is, the measuring current supply electrodes 70 and 71 are disposed on a left back portion and right back portion of the housing 78, respectively. The voltage measuring electrodes 73 and 74 are disposed on a left front portion and right front portion of the housing 78, respectively. The display 63 and the key switch 64 are disposed on the front side of the housing 78.

Figure 11:
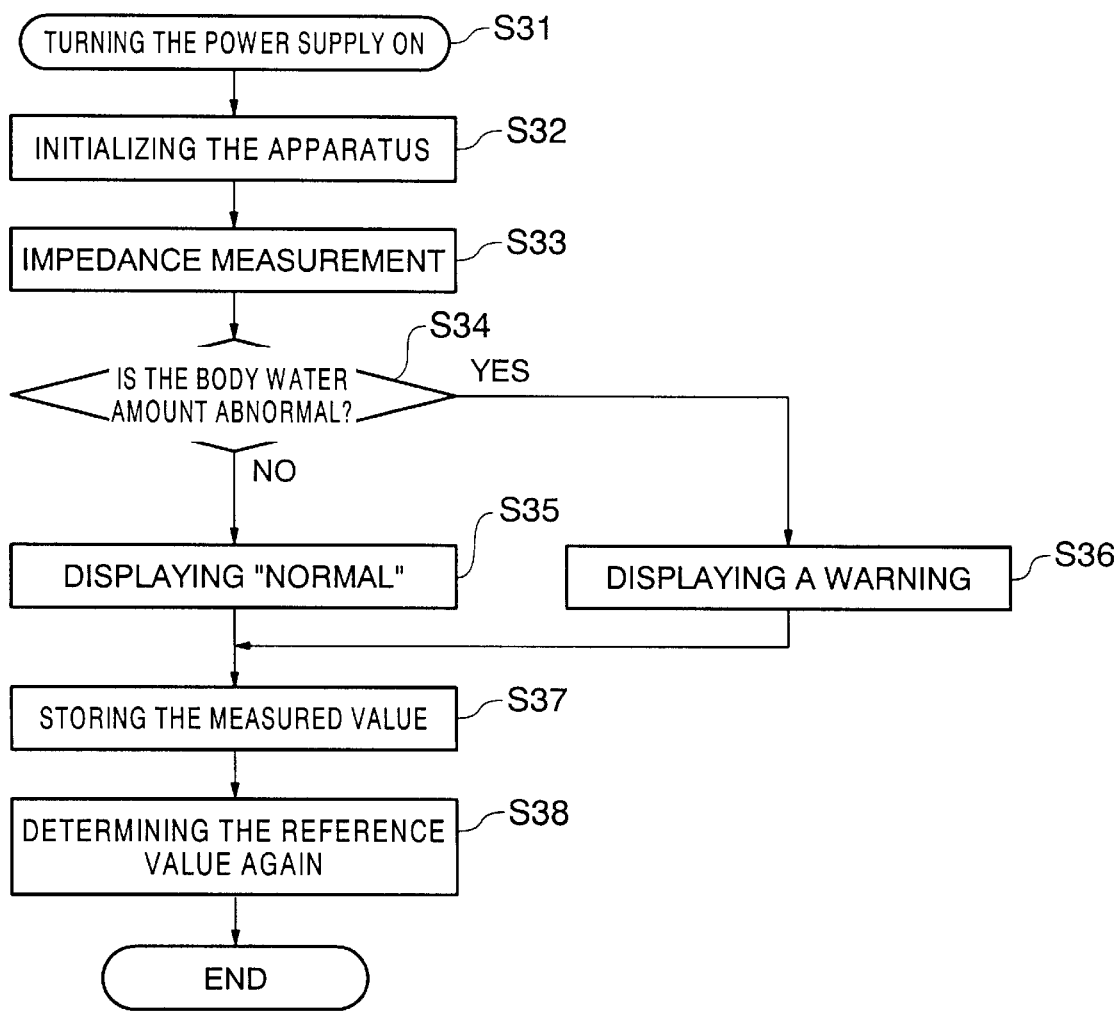
FIG. 11 is a flow chart illustrating an action flow of the body water amount condition judging apparatus shown in FIG. 9.
Figure 12:
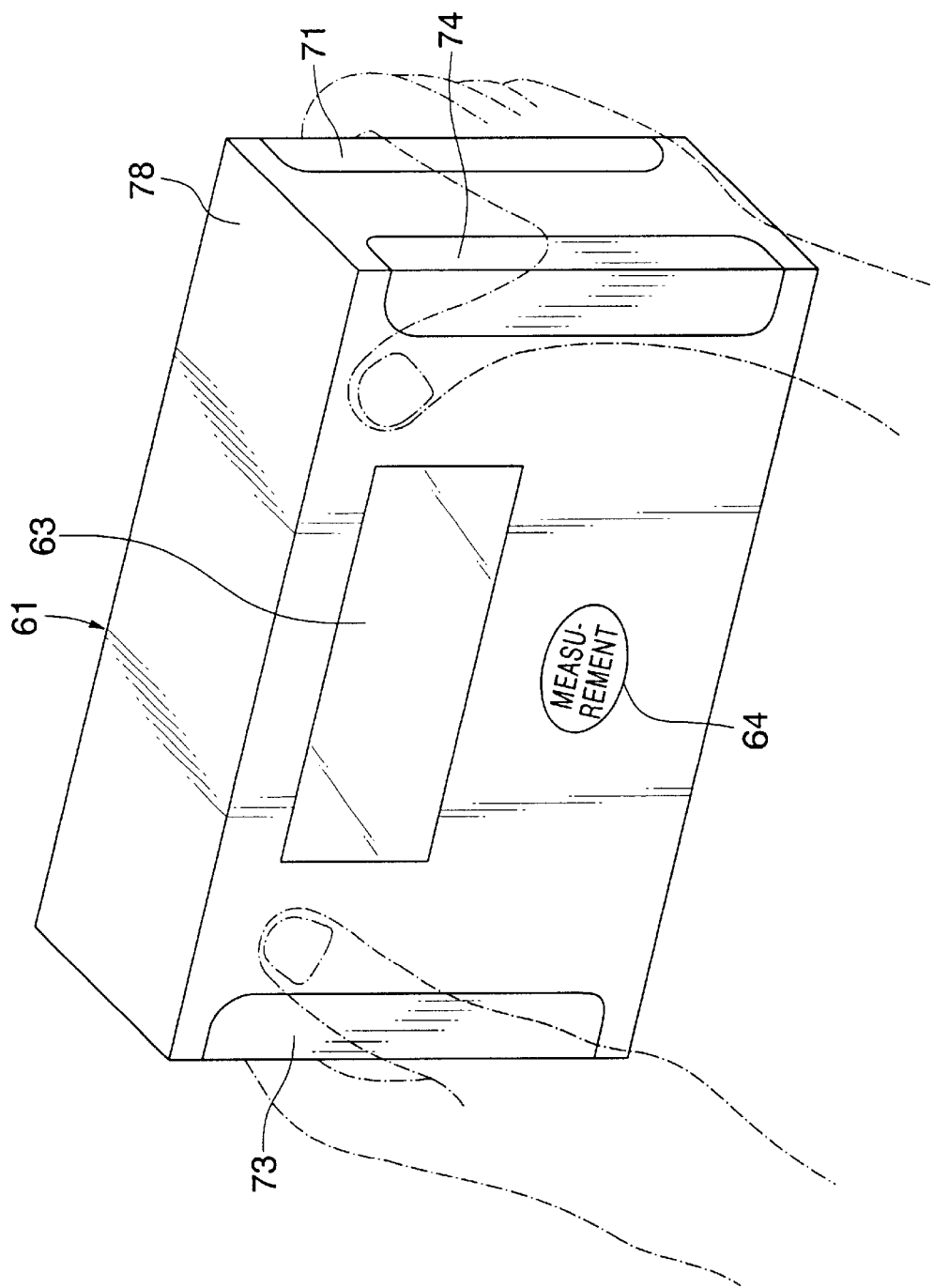
FIG. 12 is a perspective view illustrating an arrangement of hands in judging conditions using the body water amount condition judging apparatus shown in FIG. 9.

Now the operation of the apparatus will be described. FIG. 11 shows a flowchart illustrating a series of actions of the second embodiment. When the subject activates the power switch (step 31), the apparatus 61 is initialized (step 32). Then, the apparatus 61 is changed to a measuring mode. As shown in FIG. 12, the subject contacts his or her fingers other than the thumbs to the measuring current supply electrodes 70 and 71, and contacts his or her thenars to the voltage measuring electrodes 73 and 74. The subject holds the apparatus 61 in such a way, and then inputs the instruction for starting measurement through the key switch 64. When the instruction for starting measurement is input, the apparatus 61 starts to measure multi-frequency bioelectric impedance of the subject. That is, signals are directed from the microcomputer 62 to the filter circuit 67 according to measurement control parameters which are written in a ROM in the microcomputer 62 beforehand. The filter circuit 67 adjusts the waveform of the AC current to be applied to a living body. The output of the filter circuit 67 is directed to the AC current output circuit 68. The AC current output circuit 68 modifies the alternating current to a predetermined effective value. One output terminal of the AC current output circuit 68 is connected to the measuring current supply electrode 70 via the reference resistor 69. The other output terminal of the AC current output circuit 68 is connected to the measuring current supply electrode 71. Thus, an AC current is applied through the measuring current supply electrodes 70 and 71 to the subject. The potentials of the both terminals of the reference resistor 69 are detected through a pair of voltage measuring electrodes 73 and 74 during the current is applied to the subject, and the output thereof is fed to the differential amplifier 75. The differential amplifier 72 outputs potential difference values between one terminal and the other terminal of the reference resistor 69 in order to detect a current flowing into the body of the subject. On the other hand, the voltages from two points on the subject are detected by the voltage measuring electrodes 73 and 74, and then supplied to the differential amplifier 75. The differential amplifier 75 outputs potential difference values between the two points of the subject. The potential difference values from the differential amplifiers 72 and 75 are switched by the switching device 76 based on the control signals supplied by the microcomputer 62, and then these values are fed to the A/D converter 77. The A/D converter 77 converts the supplied analogue values into digital values. The output of the A/D converter 77 is then supplied to the microcomputer 62. The microcomputer 62 determines the bioelectric impedance value based on these digital values. The measurement of the bioelectric impedance is conducted for each of a plurality of frequencies in the same way as the first embodiment. And then, the apparatus 61 obtains the vector locus of bioelectric impedance, and values of R0, Rinf, Re and Ri, from the bioelectric impedance values measured for each of a plurality of different frequencies in the same way as the first embodiment (step 33).

Then, apparatus 61 judges a body water amount condition at the time when the bioelectric impedance is measured at step 7. Assuming that the extra-cellular water resistance Re and the combined intra-cellular and extra-cellular water resistance Rinf (Ri//Re) are the judging parameters, this judging operation is conducted by comparing each value of judging parameters obtained at step 33 with the reference values of judging parameters of the same kind which are stored in the auxiliary memory. The reference values of judging parameters are determined in step 38.

The apparatus 61 judges in the same way as the first embodiment, based on the relation between the intra-cellular water content and the extra-cellular water content, and the intra-cellular water resistance and the extra-cellular water resistance, and further based on the supposition that the intra-cellular water resistance is little changed at their initial stages, and then the changes begin to appear in their later stages. That is, the apparatus 61 judges that there is a tendency for dehydration in the body water amount condition, if the extra-cellular water resistance measured this time is higher than the reference value by 10% or more, and the combined resistance of the intra-cellular and extra-cellular water resistance measured this time rises a little. On the other hand, the apparatus 61 judges that there is a tendency for edema, if the extra-cellular water resistance measured this time is lower than the reference value by 10% or more, and the combined resistance of the intra-cellular and extra-cellular water resistance measured this time falls a little (step 34).

When the result judged in step 34 is in a normal state, the apparatus 61 indicates to that effect on the display 63 (step 35), and when the result judged in step 34 is in an abnormal state, the apparatus 61 indicates to that effect on the display 63 (step 36). Further, the apparatus 61 stores the measured result, calculated result, and judgement result judged in step 34 in the auxiliary memory 66 (step 37).

Next, the apparatus 61 replace the reference value of the judging parameters stored in the auxiliary memory 66 with the reference values of the judging parameters obtained this time (step 38). That concludes a series of the measurement and the judgement.

In step 38 of this embodiment, reference values of judging parameters may be obtained in the same way as the first embodiment. It is also possible to incorporate the process from step 22 through 24 of the first embodiment into step 38 of this embodiment not to use abnormal judging parameters for obtaining the reference values of judging parameters. On the contrary, in the first embodiment, the reference values may be obtained in the same way as this embodiment.

The judging parameters are not restricted to the extra-cellular water resistance and the combined resistance of the intra-cellular and extra-cellular water resistance, but at least two values selected from the intra-cellular water resistance, the extra-cellular water resistance, combined resistance of the intra-cellular and extra-cellular water resistance, and the ratio of intra-cellular and extra-cellular water, which are measured in multi-frequency bioelectric impedance measurement, may be used as judging parameters just like the first embodiment.

Further, the measurement results, calculated results, judging results and the like, may be transferred to external devices like a monitor or a printer via the external input-output interface 65, as the occasion demands.

As can be understand form the above, according to the body water amount condition judging apparatus of the present invention, at least two values selected from the intra-cellular water resistance, the extra-cellular water resistance, combined resistance of the intra-cellular and extra-cellular water resistance, and the ratio of intra-cellular and extra-cellular water, which are obtained based on the bioelectric impedance measured in multi-frequency bioelectric impedance measurement, are used as the judging parameters. Using these parameters, it is possible to judge the body water amount condition considering not only mere total body water amount condition, but also each constituent component of body water, that is, each amount condition of extra-cellular water and intra-cellular water without being affected by body temperature, and the body water amount condition can then be judged in detail accurately.

Further, the reference value of judging parameters are not determined as a common value among subjects, but determined for each subject using the past values of judging parameters obtained before. Therefore, the specific reference values of judging parameters for each subject can be obtained which are not affected by the difference among individuals. In addition, since the reference values of judging parameters are determined again in the way that these values are the average values of the judging parameter values obtained in the past including the last time and abnormal values are excluded during this procedure, according as the number of times increases, the reference values of judging parameters can be obtained which indicate more exactly the body water amount in a normal condition. Therefore, it is possible to judge the body water amount condition appropriately according to each individual subject.

In addition, as the judging parameters mentioned above can be calculated based on the bioelectric impedance, the operation of the apparatus is simplified without inputting the personal parameters such as a height, an age, a sex, a body weight, and the like.

What is claimed is:

1. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device, wherein,
  said multi-frequency bioelectric impedance measuring device supplies a plurality of alternating current of different frequencies to a body of a subject and measures a bioelectric impedance value,
  said calculating device calculates the values of each judging parameter based on the bioelectric impedance value measured,
  said reference value determining unit determines reference values for each judging parameter based on previously calculated judging parameter values for the subject of each respective judging parameter, said body water amount condition judging unit judges body water amount condition by comparing each calculated judging parameter value with the determined judging parameters of the kind, and said display device displays the judging result of said body water amount condition so judged.

2. An apparatus according to claim 1 wherein;

said calculating device further calculates at least one of the values of intra-cellular water content, extra-cellular water content and total body water content.

3. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device, wherein, said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values for the subject of each respective judging parameter, said body water amount condition judging unit judges body water amount condition by comparing each calculated judging parameter value with the determined judging parameters of the kind, and said display device displays the judging result of said body water amount condition so judged;

wherein said reference value determining unit determines that an average value of each judging parameter of the past is a reference value of a judging parameter of the same kind.

4. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device, wherein, said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values for the subject of each respective judging parameter, said body water amount condition judging unit judges body water amount condition by comparing each calculated judging parameter value with the determined judging parameters of the kind, and said display device displays the judging result of said body water amount condition so judged;

wherein said reference value determining unit determines that the latest value in judging parameters of the past is a reference value of a judging parameter of the same kind.

5. An apparatus according to any one of claim 3 and wherein;

said reference value determining unit determines a reference value of a judging parameter every time the judging parameter is calculated.

6. An apparatus according to any one of claims 3 and 4 wherein;

said reference value determining unit does not use a value of a judging parameter for determining a reference value of the judging parameter, when the value of the judging parameter is abnormal.

7. An apparatus according to claim 6 wherein;

said reference value determining unit determines that a value of a judging parameter is abnormal, when the difference between each value of the judging parameter and a reference value of the judging parameter of the same kind which is already determined exceeds the predetermined value.

8. An apparatus according to claim 6 wherein;

said reference value determining unit determines whether a value of a judging parameter is abnormal or not depending upon the time a bioelectric impedance value is determined for calculating the value of the judging parameter.

9. An apparatus according to claim 6 further comprising:

an abnormal value selecting device; wherein;

said abnormal value selecting device decides whether a subject uses a value of a judging parameter for determining a reference value or not;

said reference value determining unit determines whether the value of the judging parameter is abnormal or not responding to said abnormal value selecting device.

10. An apparatus according to claim 8 wherein;

said reference value determining unit decides that a value of a judging parameter is abnormal if the time a bioelectric impedance value is determined for calculating the value of the judging parameter about the time the subject awakens.

11. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device;

wherein said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values of each respective judging parameter, said body water amount condition judging unit judges body water amount condition by comparing each calculated judging parameter value with the determined judging parameters of the kind, said display device displays the judging result of said body water amount condition so judged, said reference value determining unit determines that an average value of each judging parameter of the past is a reference value of a judging parameter of the same kind, and said reference value determining unit does not use a value of a judging parameter for determining a reference value of the judging parameter, when the value of the judging parameter is abnormal;

the apparatus further comprising an abnormal value selecting device, wherein said abnormal value selecting device decides whether a subject uses a value of a judging parameter for determining a reference value or not, and said reference value determining unit determines whether the value of the judging parameter is abnormal or not responding to said abnormal value selecting device.

12. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device;

wherein said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values of each respective judging parameter, said body water amount condition judging unit judges body water amount condition by comparing each calculated judging parameter value with the determined judging parameters of the kind, said display device displays the judging result of said body water amount condition so judged, said reference value determining unit determines that the latest value in judging parameters of the past is a reference value of a judging parameter of the same kind, and said reference value determining unit does not use a value of a judging parameter for determining a reference value of the judging parameter, when the value of the judging parameter is abnormal;

the apparatus further comprising an abnormal value selecting device, wherein said abnormal value selecting device decides whether a subject uses a value of a judging parameter for determining a reference value or not, and said reference value determining unit determines whether the value of the judging parameter is abnormal or not responding to said abnormal value selecting device.

13. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

a multi-frequency bioelectric impedance measuring device;

a calculating device;

a reference value determining unit;

a body water amount condition judging unit; and a display device;

wherein said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values of each respective judging parameter, said body water amount condition judging unit judges body water amount condition by comparing each calculated judging parameter value with the determined judging parameters of the kind, said display device displays the judging result of said body water amount condition so judged, said reference value determining unit determines that an average value of each judging parameter of the past is a reference value of a judging parameter of the same kind, said reference value determining unit does not use a value of a judging parameter for determining a reference value of the judging parameter, when the value of the judging parameter is abnormal, said reference value determining unit determines whether a value of a judging parameter is abnormal or not depending upon the time a bioelectric impedance value is determined for calculating the value of the judging parameter, and said reference value determining unit decides that a value of a judging parameter is abnormal if the time a bioelectric impedance value is determined for calculating the value of the judging parameter about the time the subject awakens.

14. A body water amount condition judging apparatus, in which at least two values selected from intra-cellular water resistance, extra-cellular water resistance, combined resistance of the intra-cellular and extra-cellular water resistance, and a ratio of intra-cellular and extra-cellular water are judging parameters for body water amount condition, comprising:

- a multi-frequency bioelectric impedance measuring device;
- a calculating device;
- a reference value determining unit;
- a body water amount condition judging unit; and
- a display device;

wherein said multi-frequency bioelectric impedance measuring device supplies a plurality of alternating current of different frequencies to a body of a subject and measures a bioelectric impedance value, said calculating device calculates the values of each judging parameter based on the bioelectric impedance value measured, said reference value determining unit determines reference values for each judging parameter based on previously calculated judging parameter values of each respective judging parameter, said body water amount condition judging unit judges body water amount condition by comparing each calculated judging parameter value with the determined judging parameters of the kind, said display device displays the judging result of said body water amount condition so judged, said reference value determining unit determines that the latest value in judging parameters of the past is a reference value of a judging parameter of the same kind, said reference value determining unit does not use a value of a judging parameter for determining a reference value of the judging parameter, when the value of the judging parameter is abnormal, said reference value determining unit determines whether a value of a judging parameter is abnormal or not depending upon the time a bioelectric impedance value is determined for calculating the value of the judging parameter, and said reference value determining unit decides that a value of a judging parameter is abnormal if the time a bioelectric impedance value is determined for calculating the value of the judging parameter about the time the subject awakens.

* * * * *